US011298387B1

(12) United States Patent
Goodall et al.

(10) Patent No.: US 11,298,387 B1
(45) Date of Patent: Apr. 12, 2022

(54) OMEGA-3 CONTAINING COMPOSITIONS

(71) Applicant: Nooter/Eriksen, Inc., St. Louis, MO (US)

(72) Inventors: Brian L. Goodall, Bretby (GB); Dmitry Kuklev, Ann Arbor, MI (US); Glen L. Bostick, Columbia, IL (US)

(73) Assignee: Nooter/Eriksen, Inc., Fenton, MO (US)

( * ) Notice: Subject to any disclaimer, the term of this patent is extended or adjusted under 35 U.S.C. 154(b) by 0 days.

(21) Appl. No.: 16/953,978

(22) Filed: Nov. 20, 2020

(51) Int. Cl.
| | |
|---|---|
| *A61K 36/02* | (2006.01) |
| *A61K 31/202* | (2006.01) |
| *A61K 31/122* | (2006.01) |
| *A23L 33/12* | (2016.01) |
| *A23D 9/007* | (2006.01) |
| *A23D 9/04* | (2006.01) |

(52) U.S. Cl.
CPC .............. *A61K 36/02* (2013.01); *A23D 9/007* (2013.01); *A23D 9/04* (2013.01); *A23L 33/12* (2016.08); *A61K 31/122* (2013.01); *A61K 31/202* (2013.01); *A23V 2002/00* (2013.01); *A61K 2236/333* (2013.01); *A61K 2236/39* (2013.01)

(58) Field of Classification Search
CPC ...................................................... A23L 33/12
See application file for complete search history.

(56) References Cited

U.S. PATENT DOCUMENTS

| 8,115,022 B2 | 2/2012 | Kale |
|---|---|---|
| 8,153,137 B2 | 4/2012 | Kale |
| 8,318,963 B2 | 11/2012 | Kale et al. |
| 8,569,531 B2 | 10/2013 | Kale |
| 8,591,912 B1 | 11/2013 | Kadam et al. |
| 8,753,707 B2 | 6/2014 | Fichtali et al. |
| 8,828,447 B2 | 9/2014 | Soerensen et al. |
| 2012/0029184 A1 | 2/2012 | Kale |
| 2014/0242238 A1 | 8/2014 | Kadam et al. |
| 2017/0035719 A1* | 2/2017 | Waibel ..................... A23L 33/12 |
| 2017/0119005 A1 | 5/2017 | Piechocki et al. |
| 2018/0289735 A1* | 10/2018 | Hill ........................ A23K 20/10 |

FOREIGN PATENT DOCUMENTS

| RU | 2512375 C1 | 4/2014 |
|---|---|---|
| UZ | 4370 C | 7/2011 |
| WO | 2010027258 A1 | 3/2010 |
| WO | 20140105576 A1 | 7/2014 |
| WO | 2003015518 A1 | 8/2014 |
| WO | 2019095280 A1 | 5/2019 |
| WO | 2019201478 A1 | 10/2019 |

OTHER PUBLICATIONS

International Search Report for PCT/EP2020/061561 dated Aug. 19, 2021.
Written Opinion for PCT/EP2020/061561 dated Aug. 19, 2021.

\* cited by examiner

*Primary Examiner* — Qiuwen Mi
(74) *Attorney, Agent, or Firm* — Sandberg Phoenix & von Gontard P.C.

(57) ABSTRACT

The present disclosure relates to a bioavailable, oil composition wherein at least 20% by weight % of its total lipids content comprises polar lipids such as glycolipids or phospholipids, at least 30 weight % of its polar lipids comprises glycolipids, and no more than 4% by weight % of the oil composition is made up of chlorophyll species. Formulations containing and methods for producing said oil compositions from algal oils or extracts are also disclosed.

9 Claims, 4 Drawing Sheets

OMEGA-3 CONTAINING COMPOSITIONS

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND

Omega-3 oils are in high demand today due to aquaculture, fisheries and other marine sources only able to supply approximately 0.8 million tons of omega-3 fatty acids per year for human consumption. This is below the human nutritional demand of 1.4 million tons required to supply the global population with 500 mg omega-3 fatty acids daily and will be further exacerbated by population growth. Omega-3 fatty acids deficiencies have been observed worldwide and particularly affect populations located in North America, central Europe, the Middle East, India, Brazil and the United Kingdom, with regional and socioeconomic differences seen within the countries. There are three major omega-3 fatty acids found in nature. Alpha linoleic acid (ALA), with 18 carbons and 3 double bonds, can be found, e.g., in flax seeds, soybean oil and olives. Docosahexaenoic acid (DHA) with 22 carbons and 6 double bonds, important developmentally for infants, is found in mammalian (including human) breast milk, fish oil, and only grows in aquatic species (algae). Eicosapentaenoic acid (EPA), with 20 carbons and 5 double bonds, like DHA, only grows in aquatic species (algae) and can be extracted from krill or fish that eat the algae, or from algae themselves.

"Working algae", i.e., algae grown using sunlight or artificial light and photosynthesis include lipids that are polar in nature, and while bioavailable, include other components which give the oil extracted therefrom an overall, very dark, nearly black-ish, appearance, and are also highly viscous, making them resemble a tar-like black solid.

An EPA-containing composition with an elevated bioavailability, which presents as a low viscosity, low chlorophyll content light amber to dark amber colored oil for use in nutraceutical and pharmaceutical products is currently unavailable, yet highly desirable.

SUMMARY

The present disclosure relates to an elevated bioavailable, EPA-rich composition. Starting material for this composition, by way of example and not limitation, may be derived from algae. In one embodiment, a composition is disclosed including a polar lipids fraction of a concentration of total lipids of at least 20% of the total lipids by weight %; wherein the polar lipids fraction comprises at least 30% glycolipids by weight; and wherein the composition comprises no greater than 4% of its weight % as a chlorophyll concentration. In certain embodiments herein, the composition further comprises no greater than 4% of its weight % as a polysaccharide composition. Further embodiments of EPA-rich compositions with elevated bioavailability, composition profiles and resulting attributes are additionally disclosed.

The above embodiments provides an attractive composition for use in both the nutraceutical and pharmaceutical fields in terms of reduced opacity and viscosity, as well as other beneficial attributes.

The composition as described above, with its total lipids having a fraction of at least 20 wt. % polar lipids, and its polar lipids having a fraction of at least 30 wt. % glycolipids, but the composition having less than a 4 wt. % chlorophyll fraction, may further include formulations with additive non-polar lipids and/or nutraceutical oils such as DHA, or other beneficial additives as more fully described below, which also assist in providing for certain beneficial combinations of a more bioavailable, nutrient rich, lighter color, lower viscosity, oil.

The disclosure also includes a method for production of a low chlorophyll content oil composition comprising the steps of obtaining an algal paste; extraction of the algal paste with an alcohol to form an alcoholic extract of algal lipids; extraction of the obtained alcoholic extract with, e.g., an organic solvent such as the hydrocarbons hexane or heptane, to separate the fraction of non-polar lipids, transferring the alcohol layer containing pigments and polar lipids to a further stage of processing; adding water to the alcohol layer extracted, e.g., with heptane, and then its sequential extraction with, e.g., heptane, to extract the pigment fraction and separating out the polar lipid fraction. Polar lipids can then be obtained from the fraction containing them by evaporation, and pigments can also be obtained by evaporation of the fraction containing them. Polysaccharides can be obtained from the fraction containing them by subjecting the fraction to a short winterization stage. Further, chlorophyll may be removed from the fraction containing them through the use of suitable bleaching materials.

The disclosure also includes an alternative method for production of a low chlorophyll content oil composition comprising the steps of obtaining an algal oil or extract which includes both polar and non-polar lipid fractions and also has a chlorophyll concentration. The method further includes using polarity characteristics of the polar and non-polar lipid fractions to segregate polar from non-polar components in the algal oil or extract, including substantially segregating the chlorophyll concentration with the non-polar lipid fraction. Additional steps include bleaching out substantially all the chlorophyll concentration from the non-polar containing fraction; and re-combining the polar and non-polar lipid fractions to produce the low chlorophyll-content oil composition These features and other features of the present disclosure will be discussed in further detail in the following detailed description.

DETAILED DESCRIPTION

The following detailed description illustrates the claimed disclosure by way of example and not by way of limitation. This description will clearly enable one skilled in the art to make and use the claimed disclosure, and describes several embodiments, adaptations, variations, alternatives and uses of the claimed disclosure. Additionally, it is to be understood that the claimed disclosure is not limited in its application to the details and compositions specifically set forth in the following description or illustrated by means of the figures. The claimed disclosure is capable of other embodiments and of being practiced or being carried out in various ways. Also, it is to be understood that the phraseology and terminology used herein is for the purpose of description and should not be regarded as limiting.

As used herein, the term "polar lipids" means amphiphilic lipids with a hydrophilic head and a hydrophobic tail. Examples of polar lipids include phospholipids and glycolipids.

As used herein the term "non-polar lipids" means fatty molecules wherein the charge distribution is largely evenly distributed, and the molecules do not have positively and negatively charged ends. Examples of non-polar lipids include triglycerides of the various fatty acids in the oil (e.g., EPA, palmitoleic acid and others).

To produce the disclosed embodiments of oil compositions an algal extract, which presents as a dark green or even black highly viscous oil can be obtained.

Procedures for obtaining the algal biomass extract, and starting algae and extraction procedures for preparing the algal biomass can include the following steps:

Obtaining an algal paste such as a *Nannochloropsis* or *Chlorella* algal paste; extraction of the algal paste with an alcohol such as an ethyl alcohol to form an alcoholic extract of algal lipids with a low water content (forming, e.g., an ethanolic extract of *Nannochloropsis* lipids (hereinafter referred to as "EEN" for brevity); extraction of the obtained EEN with, e.g., an organic solvent such as the hydrocarbons hexane or heptane to separate the fraction of non-polar lipids (e.g., triglycerides, waxes, carotenes), thus forming a "non-polar lipid fraction (F #1 of FIG. 1) in the heptane layer. The alcohol layer contains pigments and polar lipids and can be transferred to a further stage of processing. See FIG. 1.

Figure 1:
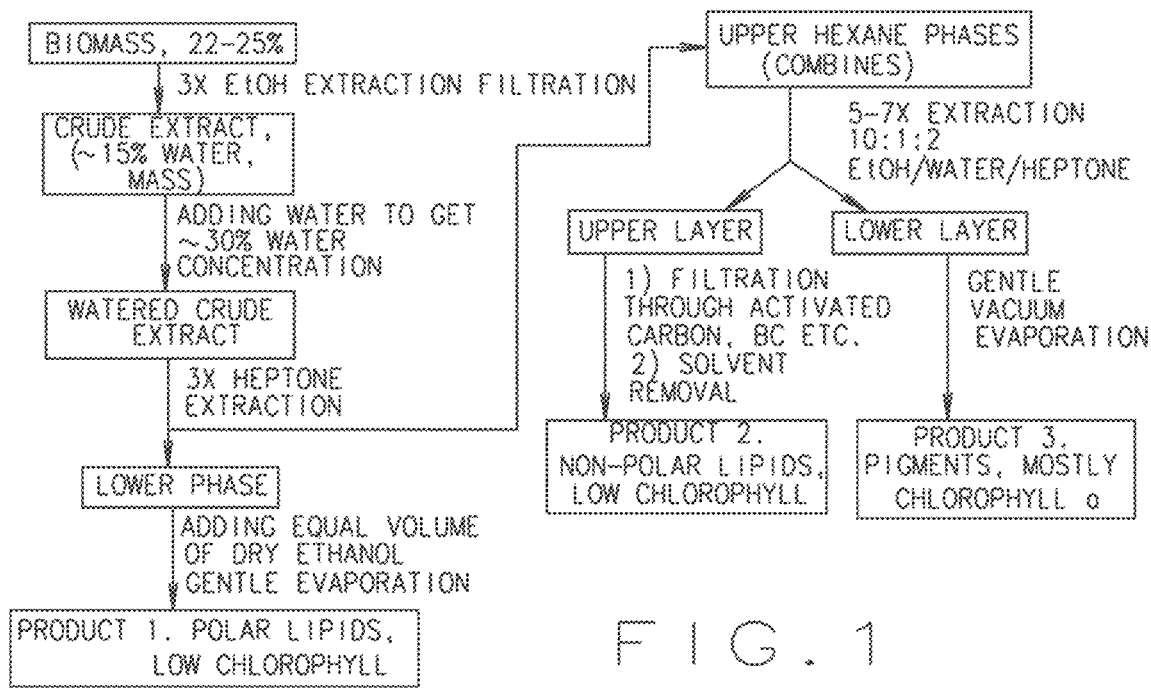
FIG. 1 discloses a schematic diagram of extraction and bleaching process steps for an exemplary method of preparation of the oil of an embodiment of the disclosure.
Figure 2:
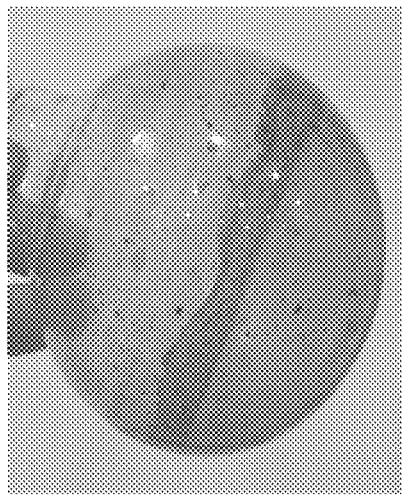
FIG. 2 is a photographic depiction of an embodiment of a composition of the disclosure having a desired target polar lipid, glycolipid and chlorophyll concentration, bioavailability, color and viscosity of an oil composition, an embodiment of which is disclosed herein.

The next stage of processing can involve adding water to the alcohol layer extracted, e.g., with heptane and then its sequential extraction with, e.g., heptane, to extract the pigment fraction (see FIG. 1, heptane layer, F #3) and separating out the polar lipid fraction (see FIG. 1, water-alcohol layer, F #2). Polar lipids can be obtained from the F #2 fraction by evaporation, and pigments can be obtained by evaporation of the F #3 fraction. The F #1 layer may contain an amount of chlorophylls and carotenoids, which can be removed by methods known to those skilled in the art, e.g., methods known for the production of edible oils. Examples of these methods include adsorption-filtration using silica gel, bleaching clays such as B80, T41, activated carbon, and others. As a result of the selective removal of chlorophyll from the F #1 fraction, in this embodiment, a largely clear to dark amber, including reddish, somewhat liquid to semi-solid oil can be obtained.

An alternative method for obtaining an algal oil or extract is disclosed in U.S. Pat. No. 8,591,912 B1 (Kiran Kadam and Brian Goodall), the contents of which are fully incorporated herein by reference.

EXAMPLES

The following examples are illustrative of the invention:

Example 1

2.1 Process Protocol for this Example (as Referred to in FIG. 1)

1) 100 g of *Nannochloropsis* algal paste (22-27% of solids in water) was weighed out. (Stage 1, FIG. 1)

2) The algae paste was placed in a 2 L flask and 850 ml of alcohol was added. (Stage 1, FIG. 1)

3) The algae was extracted for 45 min at a temperature of 70° C. with vigorous stirring. (Stage 1, FIG. 1)

4) Solid algae residues were filtered out from the ethanol extract (vacuum filtration). (Stage 2, FIG. 1)

5) The ethanol extract from the previous stage was placed into a separatory funnel (2 L), 300 mL of heptane was added to the resulting extract, stirred vigorously for 2 min, the layers were separated, the top layer was carefully selected and placed in a separate flask and about 120 mL of a green heptane layer was obtained. (Stage 3, FIG. 1)

6) Another 100 mL of heptane was added to the ethanol layer, stirred vigorously for 2 min, the layers were separated (ethanolic layer—lower, and heptane layer—upper), the top layer was carefully selected and combined with the heptane layer obtained in the previous stage (~200-220 mL of combined green heptane layers was obtained, fraction F #1). (Stage 4, FIG. 1)

7) 1 gram of silica gel was added to the entire heptane layer obtained and, after vigorous stirring for 5 minutes, the slurry was filtered through a layer of one gram of silica gel (instead of silica gel, activated carbon or T41 bleaching clay can be used). Due to variations in the properties of various silica gels, activated carbons, and bleaching clays, the actual amounts of the materials should be adjusted on plant. (Stage 8, FIG. 1)

8) The lower (ethanolic) layer was taken from this protocol stage 6, 350 mL of water and 200 mL of heptane were added, and the mixture was shaken intensively for 2 mins. After about 5 min of settling the separate phases, the top layer was carefully selected and placed in a separate flask (~400 mL of a green heptane layer was obtained at this stage). (Stage 5, FIG. 1)

9) The lower layer was repeatedly extracted from the above stage with 200 mL of heptane (3×200 mL). The top layers were carefully selected and combined with the heptane layer obtained in the previous stage. (~1000-1020 mL of combined green heptane layers was obtained, fraction F #3). (Stage 5, FIG. 1)

10) The extracted lower layer contained clarified polar lipids (F #2). This fraction can be polished by 3 g of, e.g., Amaze-N bleaching sorbent, from Helix Chromatography (15 E. Palantine Rd. #118, Prospect Heights, Ill. 60070; helixchrom.com), or similar sorbents (if needed).

11) The fractions obtained were evaporated in vacuum with heating <45° C.

Figure 4:
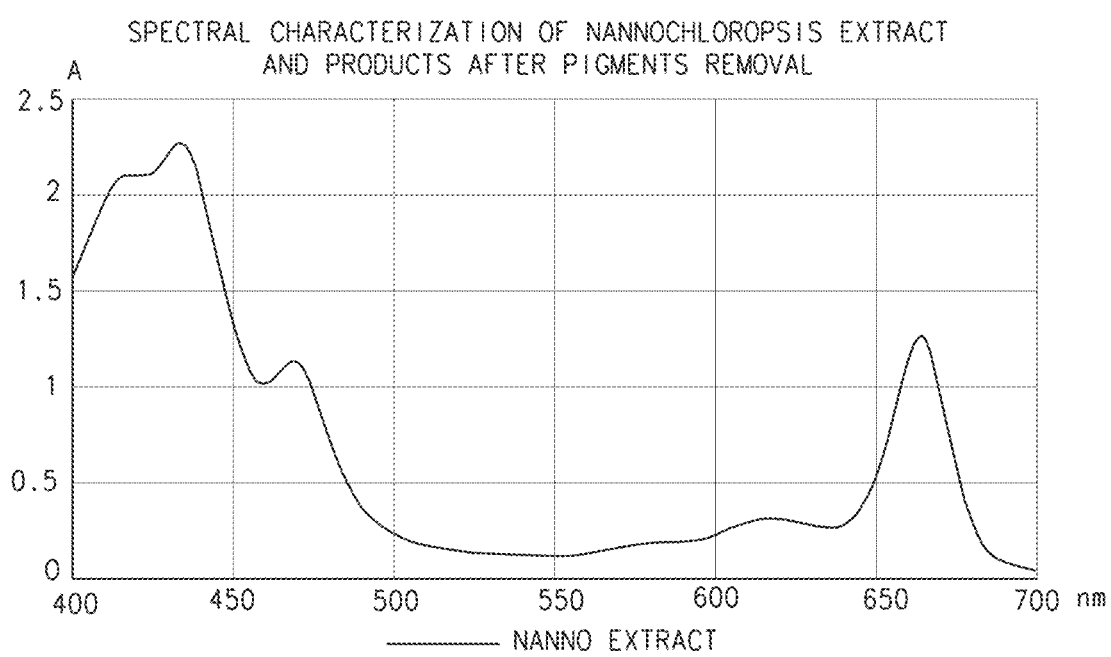
FIG. 4 is a graphical depiction of a spectral characterization of an embodiment of an ethanolic extract of *Nannochloropsis* and products after pigments removal as discussed in Example 1.

The above process steps and experimental results demonstrate a highly efficient method for a liquid-liquid extraction, removing chlorophyll and a fraction of carotenoids from algal extracts, such as for *Nannochloropsis* or *Chlorella* lipids. By use of the above embodiment of a method of the disclosure, more than 99% of chlorophylls a and b, and pheophytins were removed from an ethanolic extract of *Nannochloropsis*, as well as about two-thirds of the carotenoids (medium polarity carotenoids). See Table 2: Extraction mass balance (composition) and Table 3: Principal components of the ethanolic extract of *Nannochloropsis* for mass and weight % analysis of the compositions. See FIG. 4 for a spectral characterization of the *Nannochloropsis* ethanolic extract after removal of pigments.

TABLE 1

Extraction mass balance (composition)
Extraction Mass Balance

| Item | Value |
| --- | --- |
| Algal paste concentration, % | 27.5% |
| Initial paste mass, g | 100.0 g |
| Solid mass (recalculated), g | 27.5 g |
| Extract volume, mL | 950 |
| Extract mass, g | 9.97 |
| Concentration (mg/mL) | 10.5 |
| Extract mass, % | 36.25 |
| Residue mass, % | 63.75 |

TABLE 2

Principal components of the ethanolic extract of
Nannochloropsis Principal groups of components

| Item | Mass, g | Weight % |
| --- | --- | --- |
| Non-polar lipids | 1.533 | 15.36 |
| Medium polarity lipids | 2.605 | 26.09 |
| Chlorophyll total | 0.697 | 6.98 |
| Carotenoids total | 0.223 | 2.23 |
| Polar lipids | 3.62 | 36.23 |
| Sugars and polar components | 1.294 | 12.97 |
| Total: | 9.951 | 99.86 |

While viscosity measurements can vary depending on such factors as temperature, compositional concentrations of various ingredients in a formulation, etc., a viscosity reading taken for an embodiment of a *Nannochloropsis* extract prepared as described after combination of a polar lipids fraction with a neutral lipids fraction at 25° C. as described herein was noted to be @ 165,000 m Pa.'s.

In summary, the products shown in Example 1 can be broken down into three fractions of the incoming ethanolic extract of *Nannochloropsis*—1) Fraction (F #1), non-polar lipids, mainly triglycerides; 2) Fraction (F #2), polar lipids, including glycolipids and phospholipids; and Fraction (F #3), a fraction of medium polarity, comprising di- and mono-glycerides, free fatty acids (FFA's), carotenoids and chlorophyll. The clarified F #1 and F #2 fractions can be used as sources of valuable lipids high in palmitoleic and eicosapentaenoic acids (EPA). F #3, as a concentrate of natural pigments, including chlorophyll, astaxanthin, zeaxanthin, and others, also have value as food additives. Fractions F #1-3 can each be used as food additives and are valuable raw materials with high biological potential.

Example 2

A sample of a dark green paste of the algal biomass was prepared generally in accordance with a method outlined in U.S. Pat. No. 8,591,912 B1 (see, generally, Col. 6, line 62 to Col. 9, line 3). The algal biomass paste was extracted with hot absolute ethanol. Specifically, 66 g algal paste, 3×250 mL ethanol, at 75° C., 30' while stirring at 500 rpm each, centrifugal separation at 4450 rpm for 10 minutes, yielded a specimen algal extract.

An analysis conducted of the oil extract demonstrated the principal polar lipids in the algae specimen to be: 1) glycolipids (monogalactosyl diglycerides (MGDG) and digalactosyl diglycerides (DGDG) and 2) phospholipids (phosphatidlycholine, phosphatidylethanolamine, and phosphatidylinositol) (See Table 4, herein.)

TABLE 4

| Item | Mass, g | Weight, % | Group |
| --- | --- | --- | --- |
| Sample mass (wet algae paste) | 66.1 | n/a | Quantification |
| Dry algae (calculated) | 15.87 | 100 | Quantification |
| Dry* residue after extraction | 9.32 | 58.7 | Quantification |
| Crude extract mass | 6.56 | 41.3 | Quantification |
| Non-Lipid Components | 1.95 | 12.3 | Components |
| Non-polar lipids** | 1.11 | 7 | Lipids |
| Glycolipids*** | 1.76 | 11.1 | Lipids |
| Phospholipids**** | 0.78 | 4.9 | Lipids |
| Chlorophyll | 0.75 | 4.74 | Pigments |
| Carotenoids | 0.21 | 1.33 | Pigments |

*permanent weight on drying at room temperature (final moisture was not tested)
**TAG, DAG, FFA, Phytosterols
***Glycolipids (AMGDG, MGDG, DGDG, SQDG)
****Phospholipids (PC, PE, PI, PA, PG)

An embodiment of a bioavailable, low chlorophyll content, polar lipids-rich oil of the disclosure as quantified herein was prepared from the above starting material using the following additional steps:

1) Polar lipids were separated from a mixture of non-polar lipids, chlorophylls, and other components based on differences in polarity.

2) Chlorophylls were bleached from the remaining non-polar lipid components using well developed protocols for vegetable oil bleaching generally as described in Example 1 above; and, e.g. 1 gram of silica gel was added to the entire heptane layer obtained and, after vigorous stirring for 5 minutes, the slurry was filtered through a layer of one gram of silica gel (instead of silica gel, activated carbon or T41 bleaching clay can be used). Due to variations in the properties of various silica gels, activated carbons, and bleaching clays, the actual amounts of the materials should generally be adjusted on plant.

3) The polar lipids fraction of (1) above was combined with the bleached non-polar lipids of (2) above.

Figure 5:
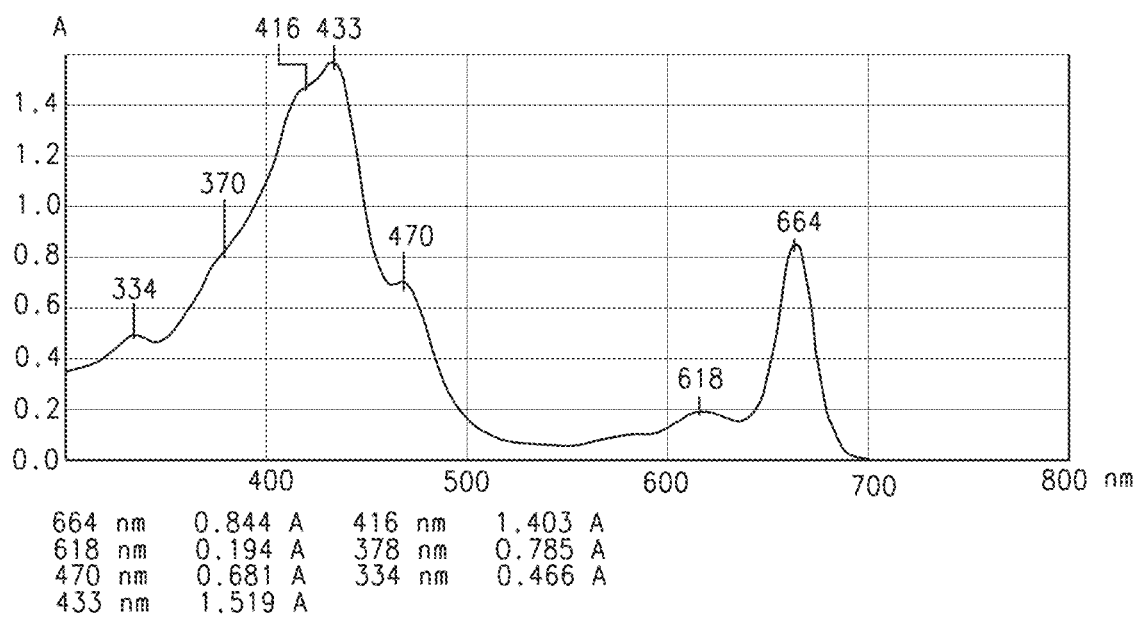
FIG. 5 is a graphical depiction of a UV-Visible spectral characterization of an embodiment of an algal extraction as discussed in Example 2.

A bioavailable polar lipid-rich, low chlorophyll-containing oil composition having a generally low viscosity and with a nearly clear to light brown color was obtained. See FIG. 5 for spectral analysis. The composition was a waxy solid at ambient temperature of @ 70 degrees Fahrenheit. The composition melts when warmed and exhibits low viscosity when blended with other oils such as triglycerides and the like.

An analysis of the oil composition of embodiments of the bioavailable oil of the disclosure made using the above processes described herein demonstrated that oils having the following components and features (column 1), and component ranges (column 2), as set forth in Table 1 were obtained:

TABLE 1

| Components/Features of Exemplary Composition | Ranges of Components of Disclosed Compositions |
|---|---|
| Total Lipid concentration in the oil product | >90% | >75% |
| Polar Lipid fraction of lipids | ~70% | >20% |
| Total Omega 3 content in oil product | ~30% | >20% |
| Total EPA content in the oil product | ~30% | >20% |
| Glycolipid concentration as % of polar lipid | ~60% | >30% |
| Glycolipid as % of oil product | ~40% | >20% |
| Phospholipid as % of polar lipid | ~40% | >20% |
| Phospholipid as % of oil product | ~25% | >10% |
| Total chlorophyll concentration in oil product | <0.1% | <4% |
| Total polysaccharide content (%) in oil product | <1% | <4% |
| Color/Capacity? | Dark Amber - Clear | Dark Amber - Clear |

Modest variations in the weight % of components and other characteristics of the oil disclosed in this application may be obtained by alterations to the process employed, as is known to those skilled in this art. However, preferably the weight % of the polar lipid fraction of the total lipid concentration of the produced oil exceeds 20%, preferably exceeds 30%, more preferably exceeds 40%, even more preferably exceeds 50%, and still more preferably is about 70% or above. Also, preferably, the weight % of the chlorophyll concentration in the oil product is less than 4% of the weight of the total oil product, more preferably, it is less than 3.0%, yet more preferably, it is less than 2.0%, even more preferably, it is less than 1.0%, and still more preferably, it is about 0.1% or below. Also, preferably, the weight % of the polysaccharides concentration in the oil product is about 4% or less of the weight of the total oil product, more preferably, it is less than 3.0%, yet more preferably, it is less than 2.0%, even more preferably, it is less than 1.0% or below. Additionally, the weight % of glycolipids as a weight % of total polar lipids exceeds 20%, preferably exceeds 30%, more preferably exceeds about 40%, even more preferably exceeds 50%, and still more preferably it is about 60% or above, and its weight % of the total oil composition exceeds 10%, more preferably 20%, and still more preferably is about 25% or above. Additionally, the weight % of phospholipids as a weight % of polar lipids exceeds 20%, more preferably exceeds 30%, and still more preferably exceeds 35%, and their weight % of the total oil composition exceeds 20%, more preferably 30%, and still more preferably 40%. While not being bound by any particular theory, applicant believes that by the combination of these characteristics, including very low chlorophyll concentration in the oil product, an attractive, lightly colored, nearly clear, to amber, up through darker amber color is produced. Also, EPA concentration of the total oil product content is at least 20 weight %, more preferably at least 25%, and still more preferably at least about 30 weight % or greater is produced. Similarly, the omega 3 content of the oil product is at least 20 weight %, more preferably at least 25 weight %, and still more preferably at least about 30 weight % or greater is produced. Elevated bioavailability of the resultant oil is also achieved.

Figure 3:
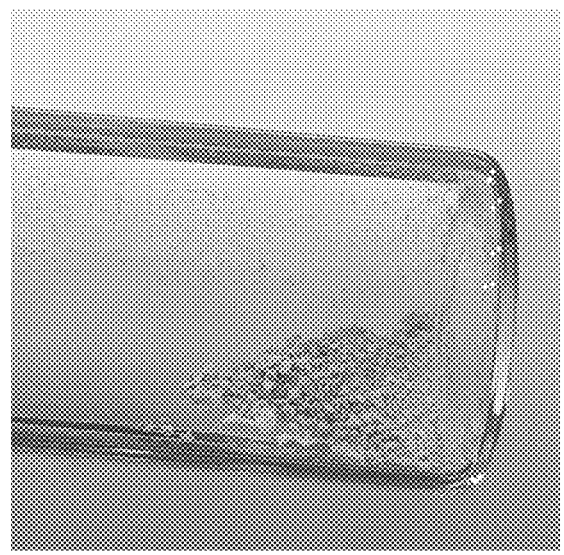
FIG. 3 is a photographic depiction of a powder obtained by an embodiment of a process of the disclosure made up substantially of non-lipids components comprising, e.g., polysaccharides contained in the crude ethanolic algal extract made according to an embodiment of the process as described herein.

Also obtained in embodiments of processes of the disclosure are powders of non-lipids components such as polysaccharides of the crude ethanolic algal extracts. See FIG. 3.

It should also be noted that for EPA-containing, high polar content oils of the disclosure, there is a greatly reduced weight % of the following chlorophylls: 1) chlorophyll a, 2) protochlorophyll a, and 3) methylchlorophyllide. Preferably, the weight % of the chlorophylls of the composition is less than 4%, preferably less than 3%, yet more preferably less than 2%, even more preferably less than 1%, still more preferably less than 0.5%, and still even more preferably less than about 0.1% of the total weight % of the composition.

In another embodiment of a composition of the disclosure, the composition has an enhanced weight % of several other ingredients, including carotenoids, e.g., carotenes (α and β), and zeaxanthins (yellow pigments), and canthaxanthin and zeaxanthin (reddish pigments), with total carotenoids making up more than 0.5% of the total weight of the extract and preferably more than 1%.

In other alternative embodiments of the disclosure, the bioavailable, high polar-lipids containing, EPA-containing, low chlorophyll content oil compositions, embodiments of which are disclosed herein, can be presented as formulations in which other useful ingredients are added. These other useful ingredients can be added alone, or in one or more combinations, e.g., combinations with other essential oils, dietary supplements, health supplements and the like. Specific examples include, but are not limited to—1) other omega 3 containing oils or components such as DHA and EPA (e.g., in the form of the neutral lipids extracted as a product in the instant invention or externally sourced), the lysolipids from the instant invention, or externally sourced, ethyl esters of DHA or EPA; 2) antioxidants such as carotenoids, including astaxanthin, lutein, zeaxanthin, lycopene, carotenes (alpha and beta), cryptoxanthin, and mixture thereof (including the carotenoid fraction of the instant invention); 3) vitamins, such as vitamin C and D; 4) cannabinoids, such as cannabidiol (CBD), and 5) other combinations. It is understood that such formulations including some of these species with less-colored and/or less-viscous compositional profiles, may reduce the overall color profile and viscosity of formulations which include the fatty acid compositions with high polar lipid, high glycolipid, and low chlorophyll concentrations prepared by embodiments of the processes disclosed herein. Thus, this may be achieved, e.g., by inclusion of non-polar lipids, either added back in from original biomass stock, or from an external source, or by preparation of formulations which demonstrate such attributes.

Examples of nutraceutical formulations including blends of the polar EPA fraction described above with DHA (omega 3) can beneficially be in a ratio from 10-90 to 90-10, wherein preferable levels of the polar EPA formulation component being mixed at 20-50%. Uses for such a formulations include both use as a key food supplement/nutraceutical in its own right for cardiovascular health, mood, anti-depression and more, and also as a delivery system for other neutral lipids and components it is formulated with. This can be DHA, other neutral forms of EPA, or mixtures thereof. Astaxanthin at levels of 10-60% can also be beneficially formulated, with preferable levels at 10-30%, either with pure polar EPA lipids or blends thereof with neutral EPA and/or EPA. Another component that could be beneficially added to such a formulation is coenzyme Q10 at levels of around 1-50%, preferably about 2-20% on the polar EPA, either pure or in any of the above formulations.

In addition to other attributes, formulation blends with added neutral lipids, e.g., can be useful to target various viscosity levels, such as 50,000 cps, preferably less than 10,000 cps, more preferably less than about 2,000 cps, and most preferably, about 300 cps or less.

In view of the above, it will be seen that the several objects and advantages of the present disclosure have been achieved and other advantageous results have been obtained.

As various changes could be made in the above constructions without departing from the scope of the disclosure, it is intended that all matter contained in the above description or shown in the accompanying drawings shall be interpreted as illustrative and not in a limiting sense.

The invention claimed is:

1. A composition comprising a concentration of total lipids, wherein at least 50% of the total lipids concentration by weight % comprises a polar lipids fraction; wherein the polar lipids fraction comprises at least 40% glycolipids as a weight % of its polar lipids fraction and the composition comprises no greater than about 0.1% of its total weight % as chlorophyll concentration.

2. A composition comprising a concentration of total lipids, wherein at least 50% of the total lipids concentration by weight % comprises a polar lipids fraction; wherein the polar lipids fraction comprises at least 40% glycolipids as a weight % of its polar lipids fraction and wherein the composition comprises no' greater than about 1% of its weight % as a chlorophyll concentration wherein the composition has a clear to dark amber color in ambient light.

3. A composition comprising a concentration of total lipids wherein at least 50% of the total lipids concentration by weight % comprises a polar lipids fraction, with greater than about 50% by weight % of the polar lipids fraction comprising glycolipids, with at least 25% of the total lipids concentration by weight % comprising an EPA concentration, and with no greater than 1% of the weight % of the composition comprising a chlorophyll concentration.

4. The composition of claim 3 wherein the composition comprises no greater than 0.5% of its weight % as chlorophyll concentration.

5. The composition of claim 4 wherein the composition comprises no greater than 0.1% of its weight % as chlorophyll concentration.

6. The composition of claim 3 wherein the composition comprises no greater than about 1% by weight % polysaccharides.

7. The composition of claim 3 wherein the composition has a clear to amber color in ambient light.

8. The composition of claim 3 wherein the composition further comprises at least about 30% of the total lipids concentration by weight % as an EPA concentration.

9. A formulation comprising:
a composition comprising a concentration of total lipids, wherein at least 20% of the total lipids concentration by weight % comprises a polar lipids fraction, with greater than about 30% by weight % of the polar lipids fraction comprising glycolipids, and wherein the composition of the formulation comprises no greater than 0.1% of its weight % as chlorophyll concentration; and,
one or more additives selected from the group consisting of:
omega 3 containing oils selected from the group consisting of oils containing one or both of ALA and DHA, antioxidants, vitamins, and cannabinoids.

* * * * *